(12) United States Patent
Lowe, III

(10) Patent No.: US 6,372,768 B2
(45) Date of Patent: Apr. 16, 2002

(54) 2-AMINOPYRIDINES CONTAINING FUSED RING SUBSTITUENTS

(75) Inventor: John A. Lowe, III, Stonington, CT (US)

(73) Assignee: Pfizer INC, New York, NY (US)

( * ) Notice: Subject to any disclaimer, the term of this patent is extended or adjusted under 35 U.S.C. 154(b) by 0 days.

(21) Appl. No.: 09/779,318

(22) Filed: Feb. 8, 2001

Related U.S. Application Data

(62) Division of application No. 09/504,989, filed on Feb. 15, 2000, now Pat. No. 6,211,208.
(60) Provisional application No. 60/121,597, filed on Feb. 25, 1999.

(51) Int. Cl.[7] .......................... A61K 31/44; C12N 9/99; C07D 213/73
(52) U.S. Cl. .................. 514/352; 435/184; 514/318; 514/255; 514/252; 546/311; 546/268.1; 546/194; 544/360
(58) Field of Search .................. 514/352, 318, 514/255, 252; 435/184; 546/311

(56) References Cited

U.S. PATENT DOCUMENTS 6,211,208 B1 * 4/2001 Lowe .................. 514/352

FOREIGN PATENT DOCUMENTS

| JP | 10001435 | 1/1998 | .......... A61K/31/44 |
| WO | WO9618616 | 6/1996 | .......... C07D/213/75 |
| WO | WO9736871 | 10/1997 | .......... C07D/213/73 |
| WO | WO9824766 | 6/1998 | |
| WO | WO9834919 | 8/1998 | .......... C07D/213/73 |
| WO | WO9910339 | 3/1999 | .......... C07D/401/10 |
| WO | WO9911620 | 3/1999 | .......... C07D/213/73 |
| WO | WO9962883 | 12/1999 | .......... C07D/213/73 |

* cited by examiner

Primary Examiner—Charanjit S. Aulakh
(74) Attorney, Agent, or Firm—Peter C. Richardson; Paul H. Ginsburg; Roy F. Waldron

(57) ABSTRACT

The present invention relates to 2-aminopyridine derivatives of the formula I:

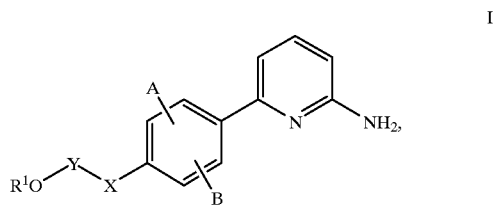

I or pharmaceutically acceptable salts thereof, wherein

A and B are each independently H, or together, A and B form a ring fused to the phenyl ring, said ring being saturated or unsaturated and containing from 5 to 7 ring member atoms, where said ring member atoms may optionally comprise from 1 to 2 heteroatoms selected independently from the group consisting of N, O or S, provided that no two adjacent ring members are heteroatoms;

X is oxygen or a single bond;

Y is $(C_1$–$C_6)$alkyl;

$R^1$ is hydrogen, $(C_1$–$C_6)$alkyl or a $(C_1$–$C_6$ alkyl) group substituted with —$NR^2R^3$ wherein $R^2$ and $R^3$ are either selected independently from the group consisting of H, alkyl, aryl, aralkyl or tetrahydronaphthalene, wherein said aryl group or said aryl moiety of said aralkyl group is phenyl or naphthyl, said alkyl group or said alkyl moiety of said aralkyl group contains from one to six carbon atoms and is straight-chained or branched, and said aryl group, said tetrahydronaphthalene or said aryl moiety of said aralkyl group is optionally substituted with from one to three of halogen, nitro, cyano, amino, $(C_1$–$C_4)$alkoxy and $(C_1$–$C_4)$alkylamino moieties, or $R^2$ and $R^3$ form, together with the nitrogen to which they are attached, a heterocyclic ring, or a cyclic or bicyclic ring which is saturated or unsaturated. The compounds of the invention have the ability to inhibit the activity of nitric oxide synthases (NOS), and hence, are useful in the treatment of diseases, conditions and disorders of the central nervous system, among others.

3 Claims, No Drawings

2-AMINOPYRIDINES CONTAINING FUSED RING SUBSTITUENTS

This application is a divisional application of Ser. No. 09/504,989, filed Feb. 15, 2000, now U.S. Pat. No. 6,211,208, which claims the benefit of U.S. provisional application Ser. No. 60/121,597, Feb. 25, 1999.

The present invention relates to certain 2-aminopyridines containing fused ring substituents that exhibit activity as nitric oxide synthase (NOS) inhibitors, to pharmaceutical compositions containing them, and to their use in the treatment and prevention of central nervous system disorders, inflammatory disorders, septic shock, obesity and other diseases, disorders and conditions.

There are three known isoforms of NOS: an inducible form (I-NOS), and two constitutive forms referred to as, respectively, neuronal NOS (N-NOS) and endothelial NOS (E-NOS). Each of these enzymes carries out the conversion of arginine to citrulline, while producing a molecule of nitric oxide (NO) in response to various stimuli. It is believed that excess nitric oxide (NO) production by NOS plays a role in the pathology of a number of disorders and conditions in mammals. For example, NO produced by I-NOS is thought to play a role in diseases that involve systemic hypotension, such as toxic shock and therapy with certain cytokines. It has been shown that cancer patients treated with cytokines such as interleukin-1 (IL-1), interleukin-2 (IL-2) or tumor necrosis factor (TNF) suffer cytokine-induced shock and hypotension due to NO produced from macrophages, i.e., inducible NOS (I-NOS) (see *Chemical & Engineering News*, December 20, p. 33, (1993)). I-NOS inhibitors can reverse this. It is also believed that I-NOS plays a role in the pathology of diseases of the central nervous system such as ischemia. For example, inhibition of I-NOS has been shown to ameliorate cerebral ischemic damage in rats (see *Am. J. Physiol.*, 268, p. R286 (1995)). Suppression of adjuvant-induced arthritis by selective inhibition of I-NOS is reported in *Eur. J. Pharmacol.*, 273, p. 15-24 (1995).

NO produced by N-NOS is thought to play a role in diseases such as cerebral ischemia, pain, and opiate tolerance. For example, inhibition of N-NOS decreases infarct volume after proximal middle cerebral artery occlusion in the rat (see *J. Cerebr. Blood Flow Metab.*, 14, p. 924-929 (1994)). N-NOS inhibition has also been shown to be effective in antinociception, as evidenced by activity in the late phase of the formalin-induced hindpaw licking and acetic acid-induced abdominal constriction assays (see *Br. J. Pharmacol.*, 110, p. 219-224 (1993)). In addition, subcutaneous injection of Freund's adjuvant in the rat induces an increase in NOS-positive neurons in the spinal cord that is manifested in increased sensitivity to pain, which can be treated with NOS inhibitors (see *Japanese Journal of Pharmacology*, 75, p. 327-335 (1997)). Finally, opioid withdrawal in rodents has been reported to be reduced by N-NOS inhibition (see *Neuropsychopharmacol.*, 13, p. 269-293 (1995)).

SUMMARY OF THE INVENTION

This invention relates to compounds of the formula I:

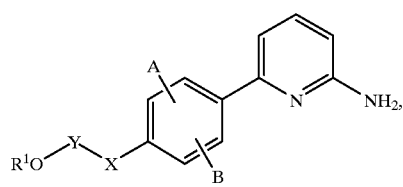

I or pharmaceutically acceptable salts thereof, wherein

A and B are each independently H, or together, A and B form a ring fused to the phenyl ring, said ring being saturated or unsaturated and containing from 5 to 7 ring member atoms, where said ring member atoms may optionally comprise from 1 to 2 heteroatoms selected independently from the group consisting of N, O or S, provided that no two adjacent ring members are heteroatoms;

X is oxygen or a single bond;

Y is $(C_1-C_6)$alkyl;

$R^1$ is hydrogen, $(C_1-C_6)$alkyl or a $(C_1-C_6$ alkyl) group substituted with $-NR^2R^3$ wherein $R^2$ and $R^3$ are either selected independently from the group consisting of H, alkyl, aryl, aralkyl or tetrahydronaphthalene, wherein said aryl group or said aryl moiety of said aralkyl group is phenyl or naphthyl, said alkyl group or said alkyl moiety of said aralkyl group contains from one to six carbon atoms and is straight-chained or branched, and said aryl group, said tetrahydronaphthalene or said aryl moiety of said aralkyl group is optionally substituted with from one to three of halogen, nitro, cyano, amino, $(C_1-C_4)$alkoxy and $(C_1-C_4)$alkylamino moieties, or $R^2$ and $R^3$-form, together with the nitrogen to which they are attached, a heterocyclic ring, or a cyclic or bicyclic ring which is saturated or unsaturated.

Preferably, the heterocyclic ring formed from $R^2$, $R^3$ and the nitrogen to which they are attached is a piperidine, azetidine, piperazine or pyrrolidine ring, optionally substituted with one or more substituents selected independently from the group consisting of $(C_1-C_6)$alkyl, amino, $(C_1-C_6)$alkylamino, [di-$(C_1-C_6)$alkyl]amino, phenyl-substituted 5- and 6-membered heterocyclic rings containing from 1 to 4 ring nitrogen atoms, benzoyl, benzoylmethyl, benzylcarbonyl, phenylaminocarbonyl, phenylethyl and phenoxycarbonyl. Preferably, the piperidine, azetidine, piperazine or pyrrolidine ring is substituted with from one to two substituents. Moreover, the phenyl moiety of any of the foregoing phenyl-containing substituents is itself optionally substituted with one or more substituents selected independently from halo, $(C_1-C_3)$alkyl, $(C_1-C_3)$alkoxy, nitro, amino, cyano, $CF_3$ and $OCF_3$; preferably with from one to two substituents.

Preferably, the cyclic or bicyclic ring formed from $R^2_1$ $R^3$ and the nitrogen to which they are attached is a 6-amino-3-azabicyclo[3.1.0]hex-3-yl ring having the formula:

wherein $R^4$ and $R^5$ are each selected independently from the group consisting of H, $(C_1-C_6)$alkyl, phenyl, naphthyl, $(C_1-C_6)$alkyl-C(=O)—, HC(=O)—, $(C_1-C_6)$alkoxy-(C=O)—, phenyl-C(=O)—, naphthyl-C(=O)—, and $R^6R^7NC(=O)$—; $R^6$ and $R^7$ are each independently hydrogen or $(C_1-C_6)$alkyl.

The present invention also relates to preferred compounds of the formula I-a:

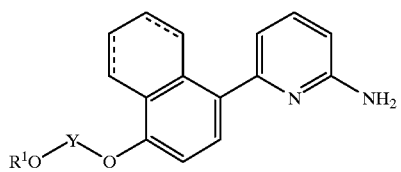

I-a wherein the broken line represents an optional double bond;

Y is $(C_1–C_6)$alkyl; and $R^1$ is hydrogen, $(C_1–C_6)$alkyl or a $(C_1–C_6$ alkyl) group substituted with —$NR^2R^3$, wherein $R^2$ and $R^3$ are as defined above.

Some preferred compounds of formula I include:

1-[4-(6-Amino-pyridin-2-yl)-naphthalen-1-yloxymethyl]-cyclohexanol;

6-[4-(2-(2-Dimethylaminoethoxy)-ethoxy)-naphthalen-1-yl]-pyridin-2-ylamine;

6-[4-(2-Hydroxy-ethoxy)-5,6,7,8-tetrahydro-naphthalen-1-yl]-pyridin-2-ylamine; and 6-[4-(2-(2-Diethylaminoethoxy)-ethoxy)-5,6,7,8-tetrahydro-naphthalen-1-yl]-pyridin-2-ylamine.

Additional compounds of formula I include:

6-[4-(2-(2-Diethylaminoethoxy)-ethoxy)-naphthalen-1-yl]-pyridin-2-ylamine;

6-[4-(2-(2-Dipropylaminoethoxy)-ethoxy)-naphthalen-1-yl]-pyridin-2-ylamine;

6-[4-(2-(2-(N-methyl, N-benzyl)aminoethoxy)-ethoxy)-naphthalen-1-yl]-pyridin-2-ylamine;

6-[4-(2-(2-(1-Piperidinyl)ethoxy)-ethoxy)-naphthalen-1-yl]-pyridin-2-ylamine; and 6-[4-(2-(2-(N-methylpiperazin-4-yl)ethoxy)-ethoxy)-naphthalen-1-yl]-pyridin-2-ylamine.

6-[4-(2-(2-(6-amino-3-azabicyclo[3.1.0] hex-2-yl)-ethoxy)-ethoxy)-naphthalen-1-yl]-pyridin-2-ylamine.

Also provided herein is a pharmaceutical composition comprising a pharmaceutically acceptable carrier and an amount of a compound of this invention effective to treat various diseases, disorders and conditions in mammals, including humans. Further provided is a method of treating various diseases, disorders and conditions in mammals, including humans, said method comprising administering to the mammals an amount of a compound of this invention effective for such treatment.

Diseases, disorders and conditions to which the compositions and methods of this invention are directed include, without limitation: acute spinal cord injuries; anxiety disorders selected from the group consisting of panic attack, agoraphobia, panic disorder with or without agoraphobia, agoraphobia without history of panic disorder, specific phobia, social phobia, obsessive-compulsive disorder, post-traumatic stress disorder and acute stress disorder; cancers, whether metastatic or not, selected from the group consisting of brain, breast, colon, lung, liver, ovarian, prostate, skin and stomach cancers, or cancers selected from the group consisting of astrocytomas, carcinomas, glioblastomas, leukemias, lymphomas, melanomas and sarcomas; cognitive disorders selected from the group consisting of amnestic disorders (e.g., amnestic disorders due to a general medical condition, substance-induced persisting amnestic disorder and amnestic disorders not otherwise specified), deliriums (e.g., deliriums due to a general medical condition, substance-induced delirium and delirium not otherwise specified), dementias (e.g., dementia of the Alzheimer's type, vascular dementia, dementia due to a general medical condition (e.g., AIDS-, Parkinson's-, head trauma-, and Huntington's-induced dementias), substance-induced persisting dementia, dementia due to multiple etiologies, and dementia not otherwise specified) and cognitive disorders not otherwise specified; emesis; epilepsy; gastrointestinal conditions selected from the group consisting of Crohn's disease, inflammatory bowel syndrome and ulcerative colitis; glaucoma; headache disorders selected from the group consisting of migraine, cluster and vascular headaches; Huntington's diseases; inflammatory disorders, either primarily inflammatory in presentation or which have, as a component of their presentation, an inflammatory phase, selected from the group consisting of adult respiratory distress syndrome (ARDS), arthritic disorders (e.g., rheumatoid and osteoarthritis), asthma, dermatological lesions, gout, inflammatory bowel disease, necrotizing vasculitides (e.g., polyarteritis nodosa, serum sickness, Wegener's granulomatosis, and Kawasaki's syndrome (Kadison)), neurogenic inflammation, psoriasis, reperfusion injury (e.g., following myocardial infarction, thrombolysis, septic shock, organ transplantation and diabetes), stroke and systemic inflammatory response syndrome; macular degeneration; obesity; neurodegenerative diseases selected from the group consisting of Alzheimer's, ALS, multiple sclerosis and Parkinson's diseases; pathological conditions selected from the group consisting of cardiomyopathy, diabetic neuropathy and diabetic nephropathy; psychotic conditions selected from the group consisting of schizophrenia (e.g., paranoid-type, disorganized-type, catatonic-type, undifferentiated-type and residual-type), schizophreniform disorder, schizoaffective disorder, delusional disorder, brief psychotic disorder, shared psychotic disorder, psychotic disorders due to a general medical condition and psychotic disorders not otherwise specified; sleep disorders selected from the group consisting of primary sleep disorders (e.g., parasomnias and dyssomnias), sleep disorders related to another mental disorder (including, without limitation, mood and anxiety disorders), sleep disorders due to a general medical condition and sleep disorders not otherwise specified; stroke; substance-abuse disorders selected from the group consisting of alcohol-related disorders, including alcohol-use (e.g., dependence and abuse) and alcohol-induced (e.g., intoxication, withdrawal, intoxication delirium, withdrawal delirium, persisting dementia, persisting amnestic, mood, anxiety, sexual dysfunction, sleep and not otherwise specified) disorders, amphetamine-related disorders, including amphetamine-use (e.g., dependence and abuse) and amphetamine-induced (e.g., intoxication, withdrawal, intoxication delirium, psychotic, mood, anxiety, sexual dysfunction, sleep and not otherwise-specified) disorders, caffeine-related disorders, such as intoxication, induced-anxiety disorder, induced-sleep disorder and disorders not otherwise specified; cannabis-related disorders, including cannabis-use (e.g., abuse and dependence) and cannabis-induced (e.g., intoxication, intoxication delirium, psychotic, anxiety and not otherwise specified) disorders, cocaine-related disorders, including cocaine-use (e.g., dependence and abuse) and cocaine-induced (e.g., intoxication, withdrawal, intoxication delirium, psychotic, mood, anxiety, sexual dysfunction, sleep and not otherwise specified) disorders, hallucinogen-related disorders, including hallucinogen-use (e.g., dependence and abuse) and hallucinogen-induced (e.g., intoxication, persisting perception, intoxication delirium, psychotic, mood, anxiety and not otherwise specified) disorders, inhalant-related disorders, including inhalant-use (e.g., dependence and abuse) and inhalant-induced (e.g., intoxication, intoxication delirium, persisting dementia, psychotic, mood, anxiety and not otherwise specified) disorders, nicotine-related disorders, such as dependence, withdrawal and not otherwise specified disorders, opioid related disorders, including opioid-use (e.g., dependence and abuse) and opioid-induced (e.g., intoxication, withdrawal, intoxication delirium, psychotic, mood, sexual dysfunction, sleep and not otherwise-specified) disorders, phencyclidine-related disorders, including phencyclidine-use (e.g., dependence and abuse) and phencyclidine-induced (e.g., intoxication, intoxication delirium, psychotic, mood, anxiety and not otherwise-specified) disorders, sedative-, hypnotic- or anxiolytic-related disorders, including sedative-use (e.g., dependence and abuse) and sedative-induced disorders (e.g., intoxication, withdrawal, intoxication delirium, withdrawal delirium, persisting dementia, persisting amnestic, psychotic, mood, anxiety, sexual dysfunction, sleep and not otherwise specified) disorders, polysubstance-related disorder, other substance dependence and abuse disorders, and other substance-induced disorders (e.g., intoxication, withdrawal, delirium, persisting dementia, persisting amnestic, psychotic, mood, anxiety, sexual dysfunction, sleep and not otherwise specified) disorders; toxemic conditions selected from the group consisting of ARDS, hypovolemic shock, neuron toxicity, septic shock and traumatic shock; traumatic conditions, including trauma to the head and chest; and, various additional diseases, disorders and conditions as well.

Additionally provided herein is a pharmaceutical composition comprising a pharmaceutically acceptable carrier and an amount of a compound of this invention effective to inhibit the activity of a nitric oxide synthase (NOS) in a mammal, including a human. Still further provided herein is a method of inhibiting the activity of a NOS in a mammal, including a human, which comprises administering to said mammal an amount of a compound of this invention effective to inhibit the activity of the NOS.

Additionally provided herein is a pharmaceutical composition for treating a disease, disorder or condition, such as those set forth above, in a mammal, including a human; said composition comprises a pharmaceutically acceptable carrier and an amount of a compound of this invention effective to inhibit the activity of a NOS in the mammal. Still further provided herein is a method of treating a mammal, including a human, afflicted with a disease, disorder or condition, including those set forth above; said method comprises administering to the mammal an amount of a compound of this invention effective for such treatment.

Acids used to prepare pharmaceutically acceptable acid addition salts of compounds of this invention from the corresponding base compounds are those acids which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [1,1-methylene-bis-(2-hydroxy-3-naphthoate)] salts.

Compounds of formula I may contain chiral centers, and therefore may exist in different enantiomeric and diastereomeric forms; this invention is directed to all such optical and stereoisomers of compounds of formula I, as well as mixtures thereof, and to all pharmaceutical compositions and methods of treatment that contain or employ them.

This invention is also directed to isotopically-labeled compounds identical to those recited in formula I but for the fact that one or more atoms are replaced therein by an atom having an atomic mass or mass number different from the atomic mass or mass number usually found in nature. Examples of isotopes that can be incorporated into compounds of this invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Compounds of formula I, prodrugs thereof, and pharmaceutically acceptable salts of said compounds, or of said prodrugs, which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful, for example, in drug and/or substrate tissue distribution assays. Tritiated, i.e., $^3H$, and carbon-14, i.e., $^{14}C$, isotopes are particularly preferred for their ease of preparation and detectability. Furthermore, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances.

Isotopically-labeled compounds of formula I of this invention and prodrugs thereof can generally be prepared by carrying out the procedures disclosed in the Schemes, and/or in the Examples, set forth below, by substituting a readily available isotopically-labeled reagent for a non-isotopically labeled reagent.

The following terms have the stated meanings throughout this application, unless otherwise indicated:

"Alkyl" refers to saturated monovalent hydrocarbon radicals having straight chain moieties, branched moieties, and in the case where the number of carbons is greater than three, cyclic moieties, and combinations thereof;

"One or more substituents" refers to a number of substituents that equals from one to the maximum number of substituents possible based on the number of available bonding sites;

"Halo" and "halogen" each refer to chloro, fluoro, bromo and iodo;

"Treating" refers to, and includes, reversing, alleviating, inhibiting the progress of, or preventing a disease, disorder or condition, or one or more symptoms thereof; and "treatment" refers to the act of treating, as defined above.

DETAILED DESCRIPTION OF THE INVENTION

Compounds of the formula I may be prepared as described in the following reaction schemes and discussion. Unless otherwise indicated, $R^1$, $R^2$, $R^3$, $R^4$, $R^5$, $R^6$ and $R^7$ and structural formula I in the reaction schemes and discussion that follow, are defined as above.

Scheme 1

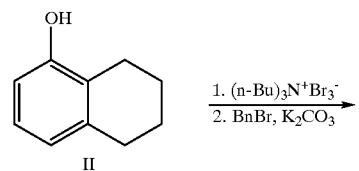

II

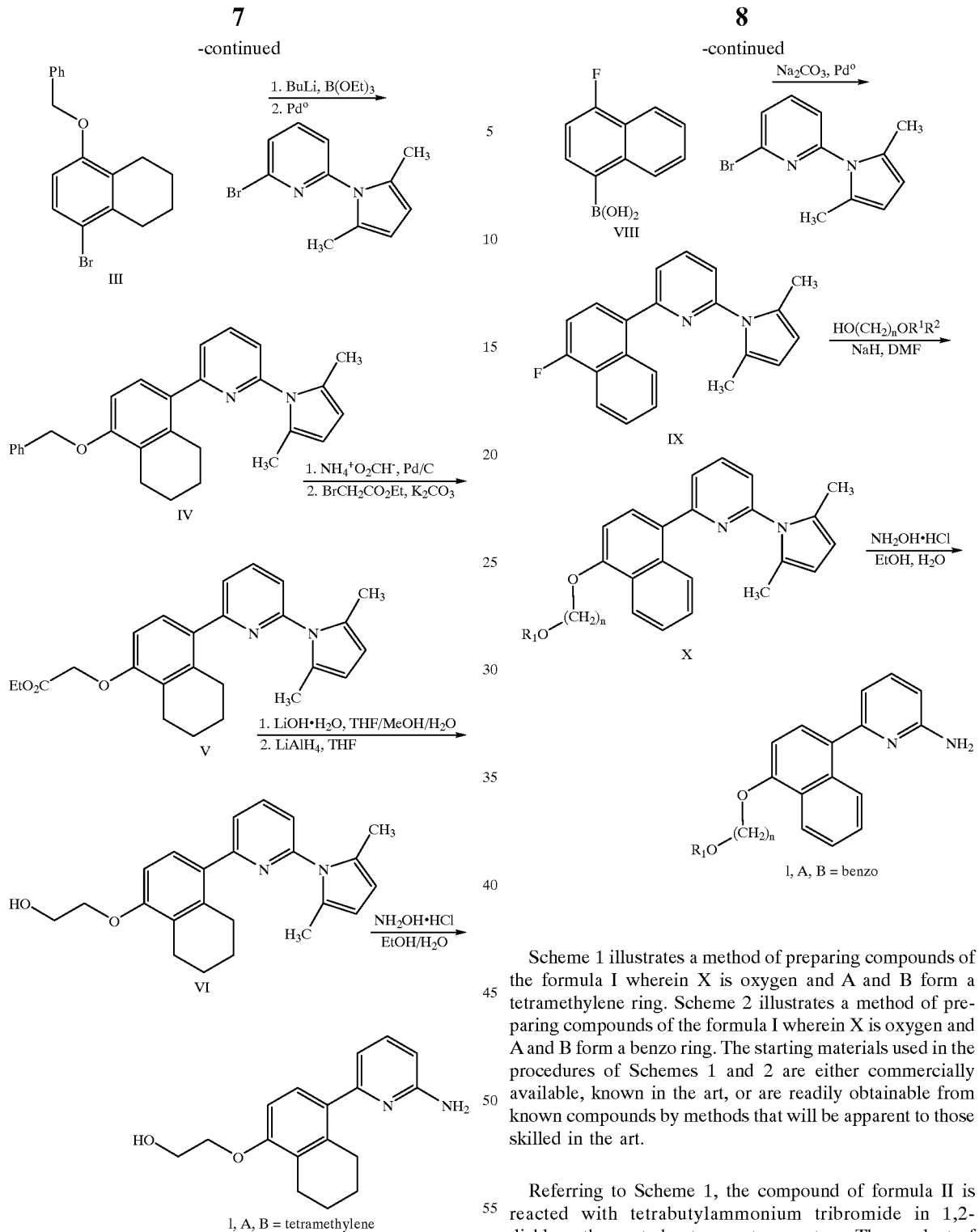

Scheme 1 illustrates a method of preparing compounds of the formula I wherein X is oxygen and A and B form a tetramethylene ring. Scheme 2 illustrates a method of preparing compounds of the formula I wherein X is oxygen and A and B form a benzo ring. The starting materials used in the procedures of Schemes 1 and 2 are either commercially available, known in the art, or are readily obtainable from known compounds by methods that will be apparent to those skilled in the art.

Referring to Scheme 1, the compound of formula II is reacted with tetrabutylammonium tribromide in 1,2-dichloroethane at about room temperature. The product of this reaction is then treated with benzyl bromide and potassium carbonate in a solvent such as acetonitrile, at about the reflux temperature of the reaction mixture, to form the compound of formula III.

The compound of formula III is then converted into 1-benzyloxy-naphthalene-4-boronic acid by the procedure described above for preparing the boronic acid derivative of formula IV in Scheme 1. Reaction of 1-benzyoxy-napthalene-4-boronic acid with 6-bromo-2-(2,5- dimethylpyrrolyl)pyridine in an ethanol solvent, in the presence of sodium carbonate and tetrakistriphenyl palladium, at about the reflux temperature of the reaction mixture, yields the compound of formula V, which can be converted into the compound of formula VI using the following two step process: the compound of formula V is reacted with ammonium formate and ten percent palladium on carbon, in an ethanol solvent, at about the reflux temperature of the reaction mixture, to yield the analogous compound to that having formula V, wherein the benzyloxy group of formula V is replaced with a hydroxy group; and, the compound of formula VI is then formed by reacting the above hydroxy derivative with 2-bromoethylacetate and potassium carbonate in acetonitrile at about the reflux temperature of the reaction mixture.

Basic hydrolysis of the compound of formula V, followed by reduction with lithium aluminum hydride or borane methyl sulfide, or other suitable metal hydrides, in tetrahydrofuran (THF) or ether, or a suitable ethereal solvent, yields the desired compound of the formula VI; the base hydrolysis is typically carried out using an alkali metal or alkaline earth metal hydroxide in a mixture of THF, methanol and water at about room temperature. The compound of formula VI can be converted into the desired compound of formula I as follows. The 2,5-dimethylpyrrolyl protecting group is removed by reaction with hydroxylamine hydrochloride. This reaction is generally carried out in an alcoholic or aqueous alcoholic solvent, at a temperature from about room temperature to about the reflux temperature of the reaction mixture, preferably at about the reflux temperature, for about 8 to about 72 hours.

Compounds of the formula I that are identical to those of formula I but for the fact that ring A is other than benzo can be prepared in an analogous fashion, starting with the appropriate compound that is analogous to that of formula II, wherein the unsubstituted benzo ring of formula II is replaced by a ring other than benzo that is within the definition of ring A.

Referring to Scheme 2, the known 1-fluoronaphthalene, compound VII, is brominated with bromine in acetic acid at a temperature from room temperature to reflux for 1 to 48 hours, and the bromide cooled to about −70° C. in dry tetrahydrofuran (THF), and then a solution of n-butyl lithium is added to it. The resulting solution is then treated with triethyl borate and allowed to warm to room temperature to form the compound of formula VIII, which is subsequently reacted with 6-bromo-2-(2,5-dimethylpyrrolyl)pyridine to form the compound of formula IX. This reaction is generally carried out in an aqueous ethanol solvent, in the presence of sodium carbonate and tetrakistriphenylphoshine palladium, at about the reflux temperature.

Compound IX is then treated with an alkali metal alkoxide, prepared from, for example, sodium hydride in a polar solvent such as dimethylformamide, at a temperature from room temperature to 140° C. for 1 to 48 hours. The resulting compound, X, is then deblocked to remove the 2,5-dimethylpyrrolyl protecting group by reaction with hydroxylamine hydrochloride. This reaction is generally carried out in an alcoholic or aqueous alcoholic solvent, at a temperature from about room temperature to about the reflux temperature of the reaction mixture, preferably at about the reflux temperature, for about 8 to about 72 hours.

The last step in each of Schemes I and II for the preparation of compounds of formula I comprises the removal of the nitrogen protecting group in the form of a 2,5-dimethylpyrrolyl ring. In general, however, compounds of formula I may be prepared by the removal of a nitrogen protecting group from a compound of formula I':

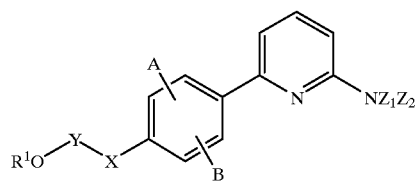

wherein $Z^1$ is hydrogen; and $Z^2$ is a nitrogen protecting group; or $Z^1$ and $Z^2$ together comprise a nitrogen protecting group. Commonly used nitrogen protecting groups include an alkylcarbonyl group such as formyl, acetyl, propionyl, etc., an alkoxycarbonyl group such as t-butoxycarbonyl, etc., an alkoxyalkylcarbonyl group such as methoxyacetyl, methoxypropionyl, etc., a substituted alkoxycarbonyl group such as trichloroethoxycarbonyl, etc., a substituted alkylcarbonyl, such as monochloromethylcarbonyl, monochloroethylcarbonyl, dichloromethylcarbonyl, dichloroethylcarbonyl, trichloromethylcarbonyl, trichloroethylcarbonyl, trichloropropylcarbonyl, etc., an aralkyloxycarbonyl group such as benzyloxycarbonyl, etc., a substituted aralkyloxycarbonyl group such as p-nitrobenzyloxycarbonyl, etc. The removal of the nitrogen protective group may be conducted, for example, by acid treatment for t-butoxycarbonyl, etc., by a treatment with zinc and an acid for trichloroethoxycarbonyl, etc. by catalytic reduction for p-nitrobenzyloxycarbonyl, etc. The protecting group, e.g., in the instance where $Z^1$ and $Z^2$ together form a nitrogen protecting group, may comprise a ring structure, such as pyrrolyl, etc., in addition to others known to those of skill in the art.

The preparation of other compounds of formula I not specifically described in the foregoing experimental section can be accomplished using combinations of the reactions described above that will be apparent to those skilled in the art. Furthermore, in each of the reactions discussed or illustrated above, pressure is not critical unless otherwise indicated. Pressures from about 0.5 atmospheres to about 5 atmospheres are generally acceptable, and ambient pressure, i.e., about 1 atmosphere, is preferred as a matter of convenience.

The compounds of formula I ("the active compounds of this invention") which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt, convert the latter back to the free base compound by treatment with an alkaline reagent, and subsequently convert the latter free base to a pharmaceutically acceptable acid addition salt. The acid addition salts of the active base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

The compounds of this invention and their pharmaceutically acceptable salts are useful as NOS inhibitors i.e., they possess the ability to inhibit the activity of NOS enzymes in mammals, including humans, and therefore, are able to function as therapeutic agents in the treatment in the mammals of various diseases, disorders and conditions characterized by excessive levels of NOS activity, including, without limitation, those diseases, disorders and conditions set forth above. The compounds' ability to inhibit NOS activity may be determined using procedures described in the literature. For example, the ability of compounds of formula I to inhibit endothelial NOS may be determined by using the procedures described by Schmidt et al. in *Proc. Natl. Acad. Sci. U.S.A.*, 88, pp. 365-369 (1991) and by Pollock et al., in *Proc. Natl. Acad. Sci. U.S.A.*, 88, pp. 10480-10484 (1991). The ability of compounds of formula I to inhibit inducible NOS may be determined using the procedures described by Schmidt et al., in *Proc. Natl. Acad. Sci. U.S.A.* 88 pp. 365-369 (1991) and by Garvey et al. in *J. Biol. Chem.*, 269, pp. 26669-26676 (1994). The ability of compounds of formula I to inhibit neuronal NOS may be determined using the procedure described by Bredt and Snyder in *Proc. Natl. Acad. Sci. U.S.A.*, 87, 682-685 (1990). The contents of these documents are incorporated herein by reference. Of four compounds of formula I that were tested, all exhibited an $IC_{50} < 10$ μM for inhibition of either inducible or neuronal NOS.

The compounds of this invention and their pharmaceutically acceptable salts can be administered via either the oral, parenteral or topical routes. In general, these compounds are most desirably administered in dosages ranging from about 0.01 to about 250 mg per day, in single or divided doses (e.g., from 1 to 4 doses per day), although variations will necessarily occur depending upon the species, weight and condition of the subject being-treated and the particular route of administration chosen. However, a dosage level that is in the range of about 0.07 mg to about 21 mg per kg of body weight per day is most desirably employed. Variations may nevertheless occur depending upon the subject being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The compounds of the invention may be administered alone or in combination with pharmaceutically acceptable carriers or diluents by either of the three routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the active compounds of the present invention topically for the treatment of conditions of the skin; this may be done by way of creams, jellies, gels, pastes, patches, ointments and the like, in accordance with standard pharmaceutical practice.

The present invention is illustrated by the following examples. It will be understood, however, that the invention is not limited to the specific details of these examples. Melting points are uncorrected. Proton nuclear magnetic resonance spectra ($^1$H NMR) and $^{13}$C nuclear magnetic resonance spectra ($^{13}$C NMR) were measured for solutions in deuterochloroform (CDCl$_3$) or in CD$_3$OD or CD$_3$SOCD$_3$ and peak positions are expressed in parts per million (ppm) downfield from tetramethylsilane (TMS). The peak shapes are denoted as follows: s, singlet; d, doublet; t, triplet; q, quartet, m, multiplet, b, broad.

EXAMPLE 1

6-[4-(2-(2-Diethylaminoethoxy)-ethoxy)-5,6,7,8-tetrahydro-naphthalen-1-yl]-pyridin-2-ylamine A. 4-Bromo-5,6,7,8-tetrahydro-1-benzyloxynaphthalene To a 250 mL round-bottomed flask equipped with addition funnel and nitrogen (N$_2$) inlet were added 2.96 g (20 mmol) 5,6,7,8-tetrahydro-naphthalen-1-ol and 50 mL 1,2-dichloroethane, and with stirring a solution of 9.64 g (20 mmol) tributylammonium tribromide in 30 mL 1,2-dichloroethane dropwise over 10 minutes. After stirring an additional 10 minutes at room temperature, the solution was washed with water, dilute aqueous sodium bisulfite, and water, dried over sodium sulfate, and evaporated. The mixture of product and tributylammonium bromide was used directly. $^1$H-NMR (δ, CDCl$_3$): 1.70 (m, 4H), 2.56 (t, J=6, 2H), 2.61 (t, J=6, 2H), 7.02 (AB, 2H), 8.0 (bs, 1H, OH); $^{13}$C-NMR (δ, CDCl$_3$): 22.2, 22.9, 23.8, 30.5, 114.0, 114.7, 126.6, 129.0, 136.7, 154.1.

The above oil was dissolved in 100 mL acetonitrile, and treated with 3.57 mL (30 mmol) benzyl bromide and 5.53 g (40 mmol) potassium carbonate, then refluxed 14 hours.

Thin layer chromatography (TLC) showed a major spot at R$_f$=0.3 in 10% methylene chloride/hexane (with benzyl bromide at R$_f$=0.4). The reaction was cooled, poured into dilute aqueous hydrochloric acid/ethyl acetate, and the organic layer separated, washed with water and brine, dried over sodium sulfate, and evaporated. The residue was chromatographed on silica gel using methylene chloride/hexane as eluant to afford 4.0 g (63%) of an oil. $^1$H-NMR (δ, CDCl$_3$): 1.77 (m, 4H), 2.75 (m, 4H), 5.045 (s, 2H), 6.62 (d, J=9, 1H), 7.3-7.5 (m, 6H); $^{13}$C-NMR (δ, CDCl$_3$): 22.2, 22.9, 24.0, 30.7, 69.9, 109.8, 116.7, 127.1, 127.9, 128.6, 129.1, 129.3, 137.2, 137.5, 155.6.

B. 5,6,7,8-tetrahydro-1-benzyloxynaphthalene-4-boronic acid

Prepared from Example 1A, using butyl lithium in tetrahydrofuran at −70° C. for 1 hour, followed by treatment with triethyl borate at −70° C. for 1 hour and room temperature for 18 hours, followed by quenching with hydrochloric acid and extraction into ethyl acetate, followed by drying over sodium sulfate and evaporation, as a white solid after trituration with hexane in 72% yield. M.p. 199–205° C.; $^1$H-NMR (δ, CDCl$_3$): 1.72 (m, 4H), 2.70 (m, 4H), 5.005 (s, 2H), 6.66 (m, 1H), 7.01 (d, J=8, 1H), 7.2–7.4 (m, 5H); $^{13}$C-NMR (δ, CDCl$_3$): 22.6, 22.9, 23.4, 30.0, 107.8, 125.9, 127.0, 127.6, 128.4, 131.1, 137.5, 140.8, 156.9.

C. 2-(2,5-Dimethylpyrrolyl)-6-[4-benzyloxy-5,6,7,8-tetrahydro-naphthalen-1-yl]-pyridine Prepared by coupling the product of Example 1B with 6-bromo-2-(2,5-dimethylpyrrolyl)pyridine in aqueous ethanol with tetrakistriphenylphosphine palladium as catalyst and sodium carbonate as the base, at reflux for 18 hours, followed by cooling, partitioning between water and ethyl acetate, drying the organic layer over sodium sulfate, and evaporation, followed by chromatography on silica gel using methanolmethylene chloride as eluant, in 100% yield as an oil. $^1$H-NMR (δ, CDCl$_3$): 1.81 (m, 2H), 1.91 (m, 2H), 2.29 (s, 6H), 2.93 (m, 4H), 5.19 (s, 2h), 6.02 (s, 2H), 6.91 (d, J=8, 1H), 7.21 (d, J=8, 1H), 7.32 (d, J=8, 1H), 7.4–7.6 (m, 6H), 7.89 (t, J=8, 1H); $^{13}$C-NMR (δ, CDCl$_3$): 13.5, 22.5, 23.0, 24.0, 28.9, 69.8, 106.8, 108.2, 119.6, 123.1, 126.8, 127.2, 127.8, 12.9, 128.6, 128.7, 132.8, 136.8, 137.6, 138.0, 151.4, 156.8, 160.4; MS (%): 409 (parent+1, 100).

D. 2-(2,5-Dimethylpyrrolyl)-6-[4-hydroxy-5,6,7,8-tetrahydro-naphthalen-1-yl]-pyridine Prepared from the product of Example 1C using ammonium formate and 10% palladium-on-carbon as catalyst, in ethanol at reflux for 3 hour, followed by cooling, filtration through Celite, evaporation, partitioning between ethyl acetate and aqueous sodium bicarbonate solution, separation, drying over sodium sulfate, and evaporation, in 100% yield as an low melting solid. $^1$H-NMR (δ, CDCl$_3$): 1.67 (m, 2H), 1.77 (m, 2H), 2.16 (s, 6H), 2.63 (m, 2H), 2.73 (m, 2H), 5.89 (s, 2H), 6.3 (bs, 1H, OH), 6.51 (d, J=8, 1H), 7.02 (d, J=8, 1H), 7.13 (d, J=8, 1H), 7.35 (d, J=8, 1H), 7.83 (t, J=8, 1H); $^{13}$C-NMR (δ, CDCl$_3$): 13.3, 22.3, 22.8 23.3, 28.6, 106.6, 112.1, 119.7, 123.3, 124.2, 127.8, 128.7, 131.9, 136.6, 138.1, 151.2, 154.4, 160.5; MS (%): 319 (parent+1, 100).

E. 2-(2,5-Dimethylpyrrolyl)-6-[4-(2-(2-diethylaminoethoxy)-ethoxy)-5,6,7,8-tetrahydro-naphthalen-1-yl]-pyridine To a three-necked 125 mL round-bottomed flask equipped with nitrogen (N$_2$) inlet and septum were added 15 mL dry dimethylformamide and 50 mg (1.3 mmol) sodium hydride (washed with hexane). The reaction was cooled to 0° C., and a solution of 200 mg (0.6 mmol) 2-(2,5-dimethylpyrrolyl)-6-[4-hydroxy-5,6,7,8-tetrahydro-naphthalen-1-yl]-pyridine in 5 mL dry dimethylformamide added dropwise. The reaction was stirred 30 min at room temperature, then a solution of 234 mg (1.3 mmol) diethylaminoethoxy-ethyl chloride (*J. Med. Chem.*, 34, 3159 (1991)) in 5 mL dry dimethylformamide added dropwise and the reaction heated at 100° C. for 20 hour, followed by more sodium hydride and chloride and heating another 24 hour The reaction was cooled, poured into aqueous sodium hydroxide solution, and extracted into ethyl acetate. The organic layer was washed with water, aqueous sodium bicarbonate solution, and brine, dried over sodium sulfate, and evaporated. The residue was chromatographed on silica gel using methanol/methylene chloride as eluant to afford 83 mg (30%) of an oil. $^1$H-NMR (δ, CDCl$_3$): 1.03 (t, J=7, 6H), 1.67 (m, 2H), 1.76 (m, 2H), 2.155 (s, 6H), 2.59 (q, J=7, 4H), 2.7–2.9 (m, 6H), 3.67 (t, J=7, 2H), 3.84 (t, J=6, 2H), 4.14 (t, J=6, 2H), 5.87 (s, 2H), 6.73 (d, J=8, 1H), 7.11 (d, J=8, 1H), 7.185 (d, J=8, 1H), 7.35 (d, J=8, 1H), 7.82 (t, J=8, 1H); $^{13}$C-NMR (δ, CDCl$_3$): 11.68, 13.33, 22.30, 22.87, 23.68, 28.66, 47.61, 52.34, 67.65, 69.67, 70.10, 106.52, 107.80, 119.48, 122.95, 126.59, 127.68, 128.62, 132.55, 136.58, 137.84, 151.21, 156.85, 160.34; MS (%): 462 (parent+1, 100).

F. 6-[4-(2-(2-Diethylaminoethoxy)-ethoxy)-5,6,7,8-tetrahydro-naphthalen-1-yl]-pyridin-2-ylamine To a 100 mL round-bottomed flask equipped with condenser and nitrogen (N$_2$) inlet were added 83 mg (0.18 mmol) 2-(2,5-dimethylpyrrolyl)-6-[4-(2-(2-diethylaminoethoxy)-ethoxy)-5,6,7,8-tetrahydro-naphthalen-1-yl]-pyridine, 250 mg (3.6 mmol) hydroxylamine hydrochloride, 10 mL ethanol, and 1 mL water. The reaction was refluxed 40 hour, cooled, and poured into 1 N hydrochloric acid. The aqueous layer was washed with ethyl acetate and adjusted to pH 12 with 6 N sodium hydroxide solution, then extracted with methylene chloride. The organic layer was dried over sodium sulfate and evaporated to afford 76 mg (100%) of an oil, which was converted to the hydrochloride salt with HCl in ether to give an amorphous tan solid. $^1$H-NMR (d, CDCl$_3$): 1.02 (t, J=7, 6H), 1.64 (m, 2H), 1.73 (m, 2H), 2.59 (q, J=7, 4H), 2.69 (m, 6H), 3.66 (t, J=7, 2H), 3.81 (t, J=5, 2H), 4.10 (t, J=5, 2H), 4.78 (bs, 2H), 6.37 (d, J=8, 1H), 6.62 (d, J=8, 1H), 6.67 (d, J=8, 1H), 7.08 (d, J=8, 1H), 7.41 (t, J=8, 1H); $^{13}$C-NMR (δ, CDCl$_3$): 11.47, 13.66, 19.90, 22.40, 22.87, 23.68, 25.47, 28.23, 31.67, 32.57, 47.49, 52.18, 67.58, 69.68, 69.87, 106.32, 107.73, 114.33, 126.41, 126.90, 133.44, 136.32, 137.87, 156.26, 156.39, 157.82, 158.61; MS (%): 384 (parent+1, 100); HRMS Calculated. for C$_{23}$H$_{34}$N$_3$O$_2$: 384.2651, Found: 384.2655.

EXAMPLE 2

6-[4-(2-Hydroxy-ethoxy)-5,6,7,8-tetrahydro-naphthalen-1-yl]-pyridin-2-ylamine

A. 2-(2,5-Dimethylpyrrolyl)-6-[4-carboethoxymethoxy-5,6,7,8-tetrahydro-naphthalen-1-yl]-pyridine Prepared from 2-(2,5-dimethylpyrrolyl)-6-[4-hydroxy-5,6,7,8-tetrahydro-naphthalen-1-yl]-pyridine (from Example 1) by alkylation with ethyl bromoacetate, using potassium carbonate, in acetonitrile. The mixture was refluxed 12 hours, cooled, poured into water, and extracted into ethyl acetate. The organic layer was washed with brine, dried over sodium sulfate, and evaporated. The residue was chromatographed on silica gel using hexane/ethyl acetate as eluant to an 83.5% yield of the product as an oil. $^1$H-NMR (δ, CDCl$_3$): 1.31 (t, J=7, 3H), 1.71 (m, 2H), 1.83 (m, 2H), 2.19 (s, 6H), 4.26 (q, J=7, 2H), 4.66 (s, 2H), 5.90 (s, 2H), 6.64 (d, J=8, 1H), 7.12 (d, J=8, 1H), 7.20 (d, J=8, 1H), 7.35 (d, J=8, 1H), 7.82 (t, J=8, 1H); $^{13}$C-NMR (δ, CDCl$_3$): 13.4, 14.2, 22.3, 22.9, 23.7, 28.7, 61.2, 65.5, 106.7, 107.8, 119.6, 123.0, 126.9, 127.7, 128.5, 133.4, 137.0, 138.1, 151.3, 156.0, 160.1, 169.0; MS (%): 405 (parent+1, 100).

B. 2-(2,5-Dimethylpyrrolyl)-6-[4-carboxymethoxy-5,6,7,8-tetrahydro-naphthalen-1-yl]-pyridine:

Prepared from Example 2A by hydrolysis in tetrahydrofuran, methanol and water using lithium hydroxide as the base at room temperature for 12 hour, followed by pouring the reaction into dilute hydrochloric acid and extraction into ethyl acetate, drying over sodium sulfate, and evaporation, in 100% yield as a solid. M.p. 199–206° C. $^1$H-NMR (δ, CDCl$_3$): 1.62 (m, 2H), 1.72 (m, 2H), 2.08 (s, 6H), 2.66 (m, 2H), 2.75 (m, 2H), 4.56 (s, 2H), 5.81 (s, 2H), 6.58 (d, J=8, 1H), 7.09 (m, 2H), 7.31 (d, J=8, 1H), 7.80 (t, J=8, 1H); $^{13}$C-NMR (δ, CDCl$_3$): 12.95, 22.1, 22.6, 23.4, 28.4, 65.0, 106.5, 107.7, 119.9, 123.3, 126.7, 127.4, 128.5, 132.8 136.6, 138.3, 151.1, 155.9, 160.1, 171.2; MS (%): 377 (parent+1, 100).

C. 2-(2,5-Dimethylpyrrolyl)-6-[4-(2-hydroxy-ethoxy)-5,6,7,8-tetrahydro-naphthalen-1-yl]-pyridine To a 100 mL round-bottomed flask equipped with condenser and nitrogen (N$_2$) inlet were added 100 mg (0.27 mmol) 2-(2,5-dimethylpyrrolyl)6-[4-carboxymethoxy-5,6,7,8-tetrahydro-naphthalen-1-yl]-pyridine (from Example 1), 20 mL dry tetrahydrofuran, and 0.6 mL (0.53 mmol) of a 1 M solution of lithium aluminum hydride in tetrahydrofuran. The reaction was refluxed 16 hour, cooled, and quenched with 1 N hydrochloric acid. The mixture was adjusted to pH 10 with 1 N aqueous sodium hydroxide solution, and extracted with ethyl acetate. The organic layer was washed with brine, dried over sodium sulfate, and evaporated. The residue of 118 mg (100%), an oil, was used directly in the following step. $^1$H-NMR (δ, CDCl$_3$): 1.69 (m, 2H), 1.78 (m, 2H), 2.16 (s, 6H), 2.7–2.9 (m, 4H), 3.95 (m, 2H), 4.08 (m, 2H), 5.885 (s, 2H), 6.73 (d, J=8, 1H), 7.13 (d, J=8, 1H), 7.20 (d, J=8, 1H), 7.35 (d, J=8, 1H), 7.83 (t, J=8, 1H); MS (%): 363 (parent+1, 100).

D. 6-[4-(2-hydroxy-ethoxy)-5,6,7,8-tetrahydro-naphthalen-1-yl]-pyridin-2-ylamine To a 100 mL round-bottomed flask equipped with condenser and nitrogen (N$_2$) inlet were added 118 mg (0.27 mmol) 2-(2,5-dimethylpyrrolyl)-6-[4-(2-hydroxy-ethoxy)-5,6,7,8-tetrahydro-naphthalen-1-yl]-pyridine, 453 mg (6.5 mmol) hydroxylamine hydrochloride, 10 mL ethanol, and 1 mL water. The reaction was refluxed 40 hour, cooled, and poured into 1 N hydrochloric acid. The aqueous layer was washed with ethyl acetate and adjusted to pH 12 with 6 N sodium hydroxide solution, then extracted with methylene chloride. The organic layer was dried over sodium sulfate and evaporated. The residue was chromatographed on silica gel using methanol/methylene chloride as eluant to afford 100 mg (100%) of an oil, which was converted to the hydrochloride salt with HCl in ether to give a solid. M.p. 170–172° C.; $^1$H-NMR (δ, CDCl$_3$): 1.65 (m, 2H), 1.75 (m, 2H), 2.67 (m, 4H), 3.88 (m, 2H), 3.90 (m, 2H), 6.38 (d, J=8, 1H), 6.62 (m, 2H), 7.08 (d, J=8, 1H), 7.42 (t, J=8, 1H); $^{13}$C-NMR (δ, CDCl$_3$): 22.27, 22.39, 22.74, 23.53, 28.11, 61.15, 68.96, 106.465, 107.655, 114.20, 126.21, 126.845, 133.395, 136.32, 137.98, 156.10, 156.53, 157.745, 158.26; MS (%): 285 (parent+1, 100); HRMS Calculated. for $C_{17}H_{21}N_2O_2$: 285.1603. Found: 285.1622.

EXAMPLE 3

6-[4-(2-(2-Dimethylaminoethoxy)-ethoxy)-naphthalen-1-yl]-pyridin-2-ylamine

A. 4-Bromo-1-fluoronaphthalene

To a 50 mL round-bottomed flask equipped with condenser and N$_2$ inlet were added 3.75 mL (5.0 g, 34.25 mmol) 1-fluoronaphthalene and 10 mL carbon tetrachloride, followed by dropwise addition of 1.7 mL (5.5 g., 34.375 mmol) bromine over 3 min. The reaction was heated to 50–60° C. as HBr was evolved for 2 hour, then cooled and concentrated. The residue was dissolved in methanol and kept overnight at 0° C. After filtration with cold methanol, the product, with melting point close to room temperature, was 4.62 g (60%) of a yellow oil. $^1$H-NMR (δ, CDCl$_3$): 7.02 (t, J=8, 1H), 7.6-7.7 (m, 3H), 8.10 (d, J=8.5, 1H), 8.20 (d, J=8.5, 1H); GCMS (%): 224/226 (parent, Br$^{79}$/Br$^{81}$ 100).

B. 4-Fluoronaphthalene-1-boronic acid

To a 250 mL three-necked round-bottomed flask equipped with septum and N$_2$ (nitrogen) inlet were added 4.62 g (20.53 mmol) 4-bromo-1-fluoronaphthalene and 100 mL dry tetrahydrofuran. The solution was cooled to −70° C., and 15.4 mL (24.64 mmol) of a 1.6 M solution of butyl lithium in hexane was added dropwise over 5 min. The reaction was stirred at −70° C. for 10 min, then 4.2 mL (3.59 g, 24.64 mmol) triethyl borate was added, and the reaction stirred at −70° C. for 20 min and warmed to room temperature. After stirring overnight at room temperature, the reaction was quenched with saturated aqueous ammonium chloride solution, acidified with 1 N hydrochloric acid, and extracted into ethyl acetate (twice). The combined organic layer was washed with brine, dried over sodium sulfate, and evaporated. The residue was triturated with hexane to give an off-white powder, 1.97 g (51%), as a mixture of monoaryl and diaryl boronic acids. $^1$H-NMR (δ, CDCl$_3$): 7.2–7.4 (m, 1H), 7.5–7.7 (m, 3H), 8.0–8.5 (m, 1H), 8.5 and 9.2 (m, 1H); APCI (−) (%): 189 (parent−1, 60).

C. 2-(2,5-Dimethylpyrrolyl)-6-(4-fluoro-naphth-1-yl)pyridine

To a 50 mL round-bottomed flask equipped with condenser and N$_2$ inlet were added 404 mg (2.13 mmol) 4-fluoronaphthalene-1-boronic acid, 534 mg (2.13 mmol) 2-(2,5-dimethylpyrrolyl)-6-bromopyridine, 902 mg (8.51 mmol) sodium carbonate, 150 mg tetrakistriphenylphosphine, 10 mL ethanol, and 2 mL water. The reaction was refluxed overnight, cooled, poured into water, and extracted into ethyl acetate. After combining with another run on a larger scale, the combined organic layer was washed with brine, dried over sodium sulfate, and evaporated. The residue was chromatographed on silica gel using hexane/ethyl acetate as eluant to afford 4.72 g (85%) of an oil. $^1$H-NMR (δ, CDCl$_3$): 2.25 (s, 6H), 5.92 (s, 2H), 7.1–7.2 (m, 2H), 7.4–7.6 (m, 4H), 7.95 (t, J=8, 1H), 8.12 (d, J=8, 1H), 8.19 (d, J=8, 1H); $^{13}$C-NMR (δ, CDCl$_3$): 13.41, 106.97, 108.82, 109.02, 120.18, 120.78, 120.84, 123.42, 123.81, 123.96, 125.48, 126.20, 127.32, 127.68, 127.76, 128.56, 132.35, 133.90, 138.22, 151.87, 157.82, 158.30, 160.34; MS (%): 317 (parent+1, 100); HRMS Calculated. for $C_{21}H_{18}N_2F$ (parent+1): 317.1454, Found: 317.1462.

D. 2-(2,5-Dimethylpyrrolyl)-6-(2-(2-dimethylaminoethoxy)-ethoxy)-naphth-1-yl)pyridine To a 20 mL round-bottomed flask equipped with condenser and nitrogen (N$_2$) inlet were added 126 mg (0.949 mmol) 2-(2-dimethylaminoethoxy)ethanol and 2 mL dry dimethylformamide, followed by 47 mg (1.187 mmol) sodium hydride (60% in oil). The reaction was heated to 70° C. to ensure complete formation of the alkoxide, and then 150 mg (0.475 mmol) 2-(2,5-dimethylpyrrolyl)-6-(4-fluoro-naphth-1-yl)pyridine in 2 mL dry dimethylformamide was added, and the reaction was heated at 80° C. for 30 min. The reaction was cooled, poured into water, and extracted into ethyl acetate. After combining with another run on a larger scale, the combined organic layer was washed with brine, dried over sodium sulfate, and evaporated. The residue was chromatographed on silica gel using methanol/methylene chloride as eluant to afford 141 mg (69%) of an oil. $^1$H-NMR (δ, CDCl$_3$): 2.24 (s, 6H), 2.32 (s, 6H), 2.61 (t, J=6, 2H), 3.76 (t, J=6, 2H), 3.98 (t, J=5, 2H), 4.35 (t, J=5, 2H), 5.90 (s, 2H), 6.89 (d, J=8, 1H), 7.21 (d, J=8, 1H), 7.49 (m, 2H), 7.56 (m, 2H), 7.91 (t, J=8, 1H), 8.11 (m, 1H), 8.36 (m, 1H); $^{13}$C-NMR (δ, CDCl$_3$): 13.45, 45.64, 58.68, 67.87, 69.33, 69.46, 104.34, 106.74, 119.71, 122.40, 123.48, 125.11, 125.20, 125.74, 126.87, 128.22, 128.59, 130.39, 131.88, 138.07, 151.68, 155.12, 159.02; MS (%): 430 (parent+1, 100); HRMS Calculated. for C$_{27}$H$_{32}$N$_3$O$_2$ (parent+1): 430.2495. Found: 430.2498.

E. 6-[4-(2-(2-Dimethylaminoethoxy)-ethoxy)-naphthalen-1-yl]-pyridin-2-ylamine

Prepared as in Example 1F, in 91% yield. M.p.: 60–75° C. (dec.), as the hydrochloride salt. $^1$H-NMR (δ, CDCl$_3$): 2.26 (s, 6H), 2.54 (t, J=6, 2H), 3.71 (t, J=6, 2H), 3.95 (t, J=5, 2H), 4.31 (t, J=5, 2H), 4.59 (bs, 2H), 6.41 (d, J=8, 1H), 6.83 (m, 2H), 7.435 (m, 4H), 8.09 (m, 1H), 8.31 (m, 1H); $^{13}$C-NMR (δ, CDCl$_3$): 45.88, 58.93, 67.96, 69.56, 69.68, 104.43, 106.54, 115.20, 122.23, 125.06, 125.68, 125.88, 126.64, 127.17, 131.60, 132.17, 137.98, 154.71, 157.77, 158.11; MS (%): 352 (parent+1, 100); Anal. Calculated. for C$_{21}$H$_{25}$N$_3$O$_2$.2HCl.¾H$_2$O.½(C$_4$H$_8$O): C 55.15, H 7.14, N 8.39. Found: C 55.31, H 7.28, N 8.64.

EXAMPLE 4

1-[4-(6-Amino-pyridin-2-yl)-naphthalen-1-yloxymethyl]-cyclohexanol

Prepared as in Example 3, using 1-hydroxy-cyclohexanemethanol, in 74% yield, as a tan powder, as the hydrochloride salt. $^1$H-NMR (δ, CDCl$_3$): 0.9–1.9 (m, 10H), 4.02 (s, 2H), 4.89 (bs, 2H), 6.54 (d, J=8, 1H), 6.87 (m, 2H), 7.5-7.6 (m, 4H), 8.10 (m, 1H), 8.31 (m, 1H); $^{13}$C-NMR (δ, CDCl$_3$): 18.98, 21.76, 25.86, 26.34, 29.68, 34.56, 60.40, 71.11, 75.75, 104.52, 107.08, 112.48, 115.21, 121.94, 125.30, 125.61, 125.77, 126.84, 127.48, 130.63, 132.08, 138.55, 154.83, 156.58, 157.79; MS (%): 349 (parent+1, 100); HRMS Calculated. for C$_{22}$H$_{23}$N$_2$O$_2$: 349.1760. Found: 349.1786.

What is claimed is:

1. A method of treating a mammal afflicted with a disease, disorder or condition which is an: acute spinal cord injury; anxiety disorder selected from the group consisting of panic attack, agoraphobia, panic disorder with or without agoraphobia, agoraphobia without history of panic disorder, specific phobia, social phobia, obsessive-compulsive disorder, post-traumatic stress disorder and acute stress disorder; cancer selected from the group consisting of brain, breast, colon, lung, liver, ovarian, prostate, skin and stomach cancers; cancer selected from the group consisting of astrocytomas, carcinomas, glioblastomas, leukemias, lymphomas, melanomas and sarcomas; cognitive disorder selected from the group consisting of amnestic disorders, deliriums, dementias, and cognitive disorders not otherwise specified; emesis; epilepsy; gastrointestinal condition selected from the group consisting of Crohn's disease, inflammatory bowel syndrome and ulcerative colitis; glaucoma; headache disorder selected from the group consisting of migraine, cluster and vascular headaches; Huntington's disease; inflammatory disorder selected from the group consisting of adult respiratory distress syndrome (ARDS), arthritic disorders, asthma, dermatological lesions, gout, inflammatory bowel disease, necrotizing vasculitides, neurogenic inflammation, psoriasis, reperfusion injury, stroke and systemic inflammatory response syndrome; macular degeneration; obesity; neurodegenerative disease selected from the group consisting of Alzheimer's, ALS, multiple sclerosis and Parkinson's; pathological condition selected from the group consisting of cardiomyopathy, diabetic neuropathy and diabetic nephropathy; psychotic condition selected from the group consisting of schizophrenia, schizophreniform disorder, schizoaffective disorder, delusional disorder, brief psychotic disorder, shared psychotic disorder, psychotic disorder due to a general medical condition and psychotic disorders not otherwise specified; sleep disorder selected from the group consisting of primary sleep disorders, sleep disorders related to another mental disorder, sleep disorders due to a general medical condition and sleep disorders not otherwise specified; stroke; substance-abuse disorder selected from the group consisting of alcohol-related disorders, amphetamine-related disorders, caffeine-related disorders, cannabis-related disorders, cocaine-related disorders, hallucinogen-related disorders, inhalant-related disorders, nicotine-related disorders, opioid-related disorders, phencyclidine-related disorders, sedative-related disorders, hypnotic-related disorders, anxiolytic-related disorders and polysubstance-related disorders; toxemic condition selected from the group consisting of ARDS, hypovolemic shock, neuron toxicity, septic shock and traumatic shock; or a traumatic condition selected from the group consisting of chest trauma and head trauma, said method comprising the administration to the mammal of a therapeutically effective amount of a compound of the formula I:

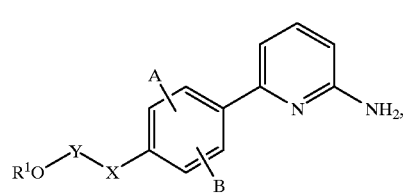

or pharmaceutically acceptable salts thereof, wherein

A and B together form a ring fused to the phenyl ring, said ring being saturated or unsaturated and containing from 5 to 7 ring member atoms, where said ring member atoms may optionally comprise from 1 to 2 heteroatoms selected independently from the group consisting of N, O or S, provided that no two adjacent ring members are heteroatoms;

X is oxygen or a single bond;

Y is (C$_1$–C$_6$)alkyl;

R$^1$ is hydrogen, (C$_1$–C$_6$ alkyl) or a (C$_1$–C$_6$ alkyl) group substituted with —NR$^2$R$^3$, wherein R$^2$ and R$^3$ are either selected independently from the group consisting of H, alkyl, aryl, aralkyl or tetrahydronaphthalene, wherein said aryl group or said aryl moiety of said aralkyl group is phenyl or naphthyl, said alkyl group or said alkyl moiety of said aralkyl group contains from one to six carbon atoms and is straight-chained or branched, and said aryl group, said tetrahydronaphthalene or said aryl moiety of said aralkyl group is optionally substituted with from one to three of halogen, nitro, cyano, amino, (C$_1$–C$_4$)alkoxy and (C$_1$–C$_4$)alkylamino moieties, or R$^2$ and R$^3$ form, together with the nitrogen to which they are attached, a heterocyclic ring, or a cyclic or bicyclic ring which is saturated or unsaturated;

effective to treat the disease, disorder or condition.

2. A method of inhibiting the activity of a NOS in a mammal which comprises the administration to the mammal of an effective amount of formula I:

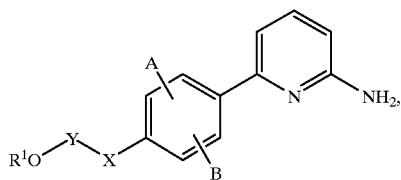

or pharmaceutically acceptable salts thereof, wherein
A and B together form a ring fused to the phenyl ring, said ring being saturated or unsaturated and containing from 5 to 7 ring member atoms, where said ring member atoms may optionally comprise from 1 to 2 heteroatoms selected independently from the group consisting of N, O or S, provided that no two adjacent ring members are heteroatoms;

X is oxygen or a single bond;

Y is $(C_1-C_6)$alkyl;

$R^1$ is hydrogen, $(C_1-C_6)$alkyl or a $(C_1-C_6$ alkyl) group substituted with —$NR^2R^3$, wherein $R^2$ and $R^3$ are either selected independently from the group consisting of H, alkyl, aryl, aralkyl or tetrahydronaphthalene, wherein said aryl group or said aryl moiety of said aralkyl group is phenyl or naphthyl, said alkyl group or said alkyl moiety of said aralkyl group contains from one to six carbon atoms and is straight-chained or branched, and said aryl group, said tetrahydronaphthalene or said aryl moiety of said aralkyl group is optionally substituted with from one to three of halogen, nitro, cyano, amino, $(C_1-C_4)$alkoxy and $(C_1-C_4)$alkylamino moieties, or $R^2$ and $R^3$ form, together with the nitrogen to which they are attached, a heterocyclic ring, or a cyclic or bicyclic ring which is saturated or unsaturated.

3. A method of treating a mammal afflicted with a disease, disorder or condition which is an: acute spinal cord injury; anxiety disorder selected from the group consisting of panic attack, agoraphobia, panic disorder with or without agoraphobia, agoraphobia without history of panic disorder, specific phobia, social phobia, obsessive-compulsive disorder, post-traumatic stress disorder and acute stress disorder; cancer selected from the group consisting of brain, breast, colon, lung, liver, ovarian, prostate, skin and stomach cancers; cancer selected from the group consisting of astrocytomas, carcinomas, glioblastomas, leukemias, lymphomas, melanomas and sarcomas; cognitive disorder selected from the group consisting of amnestic disorders, deliriums, dementias, and cognitive disorders not otherwise specified; emesis; epilepsy; gastrointestinal condition selected from the group consisting of Crohn's disease, inflammatory bowel syndrome and ulcerative colitis; glaucoma; headache disorder selected from the group consisting of migraine, cluster and vascular headaches; Huntington's disease; inflammatory disorder selected from the group consisting of adult respiratory distress syndrome (ARDS), arthritic disorders, asthma, dermatological lesions, gout, inflammatory bowel disease, necrotizing vasculitides, neurogenic inflammation, psoriasis, reperfusion injury, stroke and systemic inflammatory response syndrome; macular degeneration; obesity; neurodegenerative disease selected from the group consisting of Alzheimer's, ALS, multiple sclerosis and Parkinson's; pathological conditions selected from the group consisting of cardiomyopathy, diabetic neuropathy and diabetic nephropathy; psychotic condition selected from the group consisting of schizophrenia, schizophreniform disorder, schizoaffective disorder, delusional disorder, brief psychotic disorder, shared psychotic disorder, psychotic disorder due to a general medical condition and psychotic disorders not otherwise specified; sleep disorder selected from the group consisting of primary sleep disorders, sleep disorders related to another mental disorder, sleep disorders due to a general medical condition and sleep disorders not otherwise specified; stroke; substance-abuse disorder selected from the group consisting of alcohol-related disorders, amphetamine-related disorders, caffeine-related disorders, cannabis-related disorders, cocaine-related disorders, hallucinogen-related disorders, inhalant-related disorders, nicotine-related disorders, opioid-related disorders, phencyclidine-related disorders, sedative-related disorders, hypnotic-related disorders, anxiolytic-related disorders and polysubstance-related disorder, toxemic condition selected from the group consisting of ARDS, hypovolemic shock, neuron toxicity, septic shock and traumatic shock; or a traumatic condition selected from the group consisting of chest trauma and head trauma, said method comprising the administration to the mammal of a therapeutically effective amount of a compound of formula I:

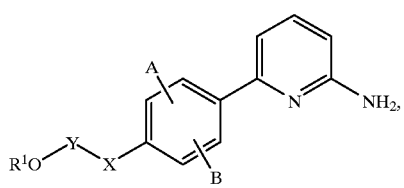

or pharmaceutically acceptable salts thereof, wherein
A and B together form a ring fused to the phenyl ring, said ring being saturated or unsaturated and containing from 5 to 7 ring member atoms, where said ring member atoms may optionally comprise from 1 to 2 heteroatoms selected independently from the group consisting of N, O or S, provided that no two adjacent ring members are heteroatoms;

X is oxygen or a single bond;

Y is $(C_1-C_6)$alkyl;

$R^1$ is hydrogen, $(C_1-C_6)$alkyl or a $(C_1-C_6$ alkyl) group substituted with —$NR^2R^3$, wherein $R^2$ and $R^3$ are either selected independently from the group consisting of H, alkyl, aryl, aralkyl or tetrahydronaphthalene, wherein said aryl group of said aryl moiety of said aralkyl group is phenyl or naphthyl, said alkyl group or said alkyl moiety of said aralkyl group contains from one to six carbon atoms and is straight-chained or branched, and said aryl group, said tetrahydronaphthalene or said aryl moiety of said aralkyl group is optionally substituted with from one to three of halogen, nitro, cyano, amino, $(C_1-C_4)$alkoxy and $(C_1-C_4)$alkylamino moieties, or $R^2$ and $R^3$ form, together with the nitrogen to which they are attached, a heterocyclic ring, or a cyclic or bicyclic ring which is saturated or unsaturated;

effective to inhibit the activity of a NOS in the mammal.

* * * * *